June 8, 1965 F. W. ANDERSON Plant Pat. 2,533
PEACH TREE
Filed March 26, 1964
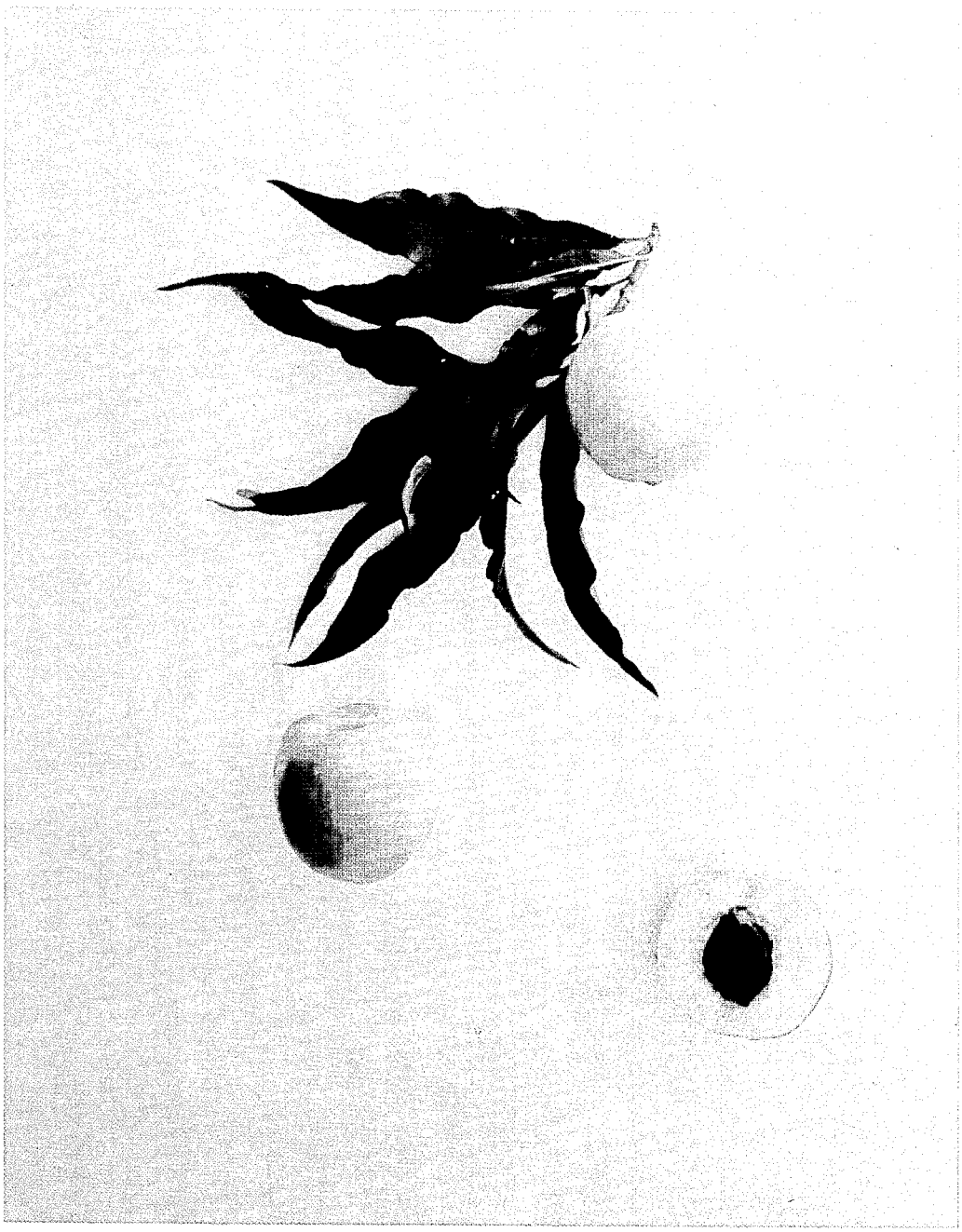
INVENTOR
*Frederic W. Anderson*
*Webster & Webster*
ATTYS.

United States Patent Office

Plant Pat. 2,533
Patented June 8, 1965

2,533
PEACH TREE

Frederic W. Anderson, Merced, Calif., assignor to L. E. Cooke Co., San Gabriel, Calif., a corporation Filed Mar. 26, 1964, Ser. No. 355,135
1 Claim. (Cl. Plt.—43)

This invention relates to a new and distinct variety of peach tree primarily characterized by its genetically dwarf size, together with the regular and productive bearing of normal size fruit having yellow skin substantially overspread with red, yellow flesh, and a clingstone; the variety being well adapted for growing both as an ornamental tree and for the production of fruit for home and local use.

By reason of short internodes, the tree of the present variety is less than one-half the height of a normal peach tree, and the leaves and fruit are much closer together than normally.

The present variety of peach tree most closely resembles the dwarf Golden Glory (United States Plant Patent No. 2,418), but in comparison bears firmer, earlier ripening fruit which is clingstone instead of freestone; the fruit having a ripening period about three weeks earlier than said Golden Glory, and the firmness of the fruit assuring of better handling and keeping qualities.

The herein claimed variety was originated by me in my experimental orchard located near Le Grand, Merced County, California, during a long term plant breeding program; the object of which program was the origination of fruit trees, including peach trees, of such small or dwarf size that, in addition to ornamental value, pruning, thinning, and harvesting operations could be conducted mainly without the use of ladders and by a person standing on the ground adjacent the tree.

Origination of the variety, under close and careful observation, was accomplished by me in the following manner:

All the flowers on a number of Flory (unpatented) dwarf peach trees were crossed with pollen from the Red Grand (United States Plant Patent No. 1,060) nectarine, and the resultant seed was planted; the trees grown from such seeds all having produced normal size peach trees which bore white fleshed fruit. Seed from these first generation peach trees were planted, and the trees grown therefrom evidenced great variation. More particularly, about three-fourths were normal in size and one-fourth dwarf; about three-fourths of both the normal size and dwarf trees produced peaches, and the other one-fourth produced nectarines; and about three-fourths of both said peach and nectarine trees produced white fleshed fruit, and the other one-fourth produced yellow fleshed fruit. The instant variety is a selection of one of such dwarf peach trees which bore yellow fleshed clingstone fruit; the variety having been selected by me, for subsequent asexual reproduction, upon the recognition of its commercial potential as a combination ornamental and fruit tree.

Thereafter, asexual reproduction of the variety was accomplished by me in my experimental orchard, located as aforesaid, by top-working on mature orchard trees; such reproductions having run true to the parent tree in all respects.

The drawing is an illustration, by photographic reproduction in color and at the time of harvest, of a twig with leaves and fruit, and one-half of another fruit cut to show the flesh and with the stone remaining in place.

Referring now more specifically to the pomological details of this new and distinct variety of peach tree, the following is an outline description thereof; all major color plate identifications being by reference to Maerz and Paul Dictionary of Color, except where common terms of color definition are employed.

Tree:
- *Size.*—Medium to small, genetically dwarf. Average height—5 to 8 feet.
- *Growth.*—Spreading.
- *Density*—Dense.
- *Production.*—Productive.
- *Bearing.*—Regular bearer.

Trunk:
- *Size.*—Stocky.
- *Texture*—Shaggy.

Branches:
- *Size.*—Stocky.
- *Texture.*—Shaggy.

Leaves:
- *Size.*—Large. Average length—6½". Average width—13/16".
- *Margin.*—Crenate.
- *Petiole.*—Short; medium thickness.
- *Glands.*—Average number and position—2 or 3 on petiole and 2 or more on blade. Alternate; medium size; reniform.
- *Color.*—Top side—medium green (23–L–8). Under side—lighter green (22–L–7).

Flower buds:
- *Size.*—Medium.

Flowers:
- *Blooming period.*—Date of first bloom—March 3, 1963. Date of full bloom—March 18, 1963. Medium, as compared with other varieties.
- *Size.*—Large.
- *Fertility.*—Self fertile, with red anthers before dehiscence.

Fruit:
- *Maturity when described.*—Eating ripe—August 8, 1963.
- *Date of first picking.*—July 28, 1963.
- *Date of last picking.*—August 8, 1963.
- *Size.*—Medium. Average diameter axially—2⅜". Average transversely in suture plane—2 5/16".
- *Form.*—Uniform; symmetrical; globose.
- *Suture.*—Distinct but shallow.
- *Ventral surface.*—Rounded slightly.
- *Cavity.*—Circular. Average depth—5/16". Average breadth—⅜".
- *Base.*—Truncate.
- *Apex.*—Short mammiform.
- *Pistil point.*—Oblique.

Skin:
- *Thickness.*—Medium.
- *Tendency to crack.*—None.
- *Down.*—Medium.
- *Color.*—Yellow (9–K–3) substantially overspread with red (6–L–4) shading darker to (7–J–5).

Flesh:
- *Texture.*—Soft; melting.
- *Ripens.*—Evenly.
- *Flavor.*—Subacid to mild.
- *Eating quality.*—Fair to good.
- *Color.*—Yellow (10–L–6). Surface of pivot cavity—red, with yellow fibers.

Stone:
- *Type.*—Cling.
- *Size.*—Medium. Average length—1¼". Average breadth—1⅛". Average thickness—¾".
- *Tendency to split.*—Slight.
- *Color.*—Purplish tone of brown (56–L–2).

Use: Home; local market.
Keeping quality: Medium.
Shipping quality: Medium.

The tree and its fruit herein described may vary in slight detail due to climatic and soil conditions under which the variety may be grown; the present description being of the variety as grown in the Central Valley of California.

The following is claimed:

A new and distinct variety of genetically dwarf peach tree, substantially as illustrated and described, characterized by short internodes and an average height of five to eight feet; by the regular and productive bearing of normal size yellow fleshed fruit having yellow skin substantially overspread with red; and, in comparison to the dwarf Golden Glory, by firmer fruit which ripens about three weeks earlier and is of clingstone instead of freestone type.

No references cited.

ABRAHAM G. STONE, *Primary Examiner.*